US00PP23403P2

(12) United States Plant Patent
Petit

(10) Patent No.: US PP23,403 P2
(45) Date of Patent: Feb. 19, 2013

(54) ***HEMEROCALLIS* PLANT NAMED 'SPD 06-12'**

(50) Latin Name: ***Hemerocallis* hybrid**
Varietal Denomination: SPd 06-12

(76) Inventor: Ted L. Petit, McIntosh, FL (US)

( * ) Notice: Subject to any disclaimer, the term of this patent is extended or adjusted under 35 U.S.C. 154(b) by 112 days.

(21) Appl. No.: 13/134,127

(22) Filed: May 31, 2011

(51) Int. Cl.
*A01H 5/00* (2006.01)

(52) U.S. Cl. ..... Plt./312

(58) Field of Classification Search ..... Plt./312
See application file for complete search history.

*Primary Examiner* — June Hwu
(74) *Attorney, Agent, or Firm* — Penny J. Aguirre

(57) ABSTRACT

A new cultivar of *Hemerocallis* named 'SPd 06-12', characterized by its flowers that are burgundy rose in color with darker burgundy eyezones with yellow-green throats, its flowers that fully open under cool growing conditions and are self cleaning, its flower petals that are broadly elliptic in shape and heavy in substance with lightly ruffled edges, its blooming habit that commences very early in the season with continuous rebloom until frost on recurrent, branched scapes with high bud counts, its foliage that is evergreen, semi-evergreen or dormant depending on the growing climate with suitability in a variety of growing climates, its compact plant habit with grass-like foliage, its fast multiplication rate, and its hardiness at least in U.S.D.A. Zones 4 to 11, and its high tolerance to daylily rust.

2 Drawing Sheets

Botanical classification: *Hemerocallis* hybrid.
Cultivar designation: 'SPd 06-12'.

CROSS REFERENCE TO A RELATED APPLICATION

This application is co-pending with U.S. Plant Patent Application and Patents filed for plants derived from the same breeding program that are entitled *Hemerocallis* Plant Named 'Spd 06-02' (U.S. Plant Pat. No. 22,181), *Hemerocallis* Plant Named 'Spd 06-01' (U.S. Plant Pat. No. 23,096), *Hemerocallis* Plant Named 'Spd 06-08' (U.S. Plant patent application Ser. No. 13/134,126), *Hemerocallis* Plant Named 'Spd 06-11' (U.S. Plant Pat. No. 23,095), *Hemerocallis* Plant Named 'Spd 06-13' (U.S. Plant Pat. No. 23,112), and *Hemerocallis* Plant Named 'Spd 06-16' (U.S. Plant Pat. No. 23,113).

BACKGROUND OF THE INVENTION

The present invention relates to a new and distinct cultivar of *Hemerocallis* plant of hybrid origin, botanically known as *Hemerocallis* 'SPd 06-12' and will be referred to hereafter by its cultivar name, 'SPd 06-12'.

The new cultivar was developed through an on-going breeding program conducted by the Inventor in McIntosh, Fla. The objectives of the breeding program are to develop new cultivars of tetraploid *Hemerocallis* that exhibit early and continuous flowering on recurrent, branched scapes with high bud counts and flowers that fully open during cool conditions, have bright flower color, heavy petal substance, and clean shedding of the old flowers to allow new buds to fully develop. Further objectives of the breeding program include developing plants that exhibit a high multiplication rate, short blooms stalks, foliage that is grass-like and compact, cold and heat hardiness and resistance to daylily rust.

The Inventor made crosses in summer of 2005 between select unnamed proprietary plants in his breeding line and pooled all the resulting seed from his crosses and evaluated the resulting seedlings based on the objectives of the breeding program. 'SPd 06-12' was selected as a single unique plant from the resulting seedlings in summer of 2006. The specific parents are unknown.

Asexual reproduction of the new cultivar was first accomplished by division in McIntosh, Fla. in 2006 by the Inventor. Propagation by division and tissue culture has determined that the characteristics of this cultivar are stable and are reproduced true to type in successive generations.

SUMMARY OF THE INVENTION

The following traits have been repeatedly observed and represent the characteristics of 'SPd 06-12'. These attributes in combination distinguish 'SPd 06-12' as a new and distinct cultivar of *Hemerocallis*.

1. 'SPd 06-12' exhibits flowers that are about 10 cm in diameter (4 inches) and are burgundy rose in color with darker burgundy eyezones with yellow-green throats.
2. 'SPd 06-12' exhibits flower petals that are broadly elliptic in shape, heavy in substance, and have lightly ruffled edges.
3. 'SPd 06-12' exhibits a blooming habit that commences very early in the season with continuous rebloom until frost on recurrent, branched scapes with high bud counts.
4. 'SPd 06-12' exhibits flowers that fully open under cool growing conditions and cleanly shed spent flowers to allow new buds to fully develop.
5. 'SPd 06-12' has foliage that is evergreen, semi-evergreen or dormant depending on the growing climate, which allows its suitability to a variety of growing climates.
6. 'SPd 06-12' is a tetraploid.
7. 'SPd 06-12' exhibits a compact plant habit with grass-like foliage with short blooms scapes that allow for ease of transporting of finished plants.
8. 'SPd 06-12' is readily propagated by division or tissue culture and exhibits a fast multiplication rate (fan increase).

9. 'SPd 06-12' is cold and heat hardy at least in U.S.D.A. Zones 4 to 11.
10. 'SPd 06-12' exhibits a very high tolerance to daylily rust (*Puccinia hemerocallidis*).

The new cultivar can be most closely compared to the cultivars 'Hawaiian Party Dress' (not patented) and 'Preppy Pink' (not patented). Both cultivars are similar to 'SPd 06-12' in flower coloration. 'Hawaiian Party Dress' differs from 'SPd 06-12' in being a diploid, in having taller flower scapes, in having foliage that is more resistant to rust, in having less flowers that do not open fully in cold weather, in commencing bloom later in the season with less recurrent blooming, and in having a slower multiplication rate. 'Preppy Pink' differs from 'SPd 06-12' in having much taller flower scapes, in having foliage that is wider and more resistant to rust, in having less flowers that are smaller in size and do not open fully in cold weather, in commencing bloom later in the season with less recurrent blooming, and in having a slower multiplication rate. 'SPd 06-12' can also be most closely compared to cultivars from the same breeding program. These cultivars differ from 'Spd 06-12' primarily in flower coloration. 'SPd 06-02' exhibits flowers that are golden yellow in color with maroon to burgundy red eyezones, 'SPd 06-01' exhibits flowers that are coral pink in color with rosy-red eyezones, 'SPd 06-08' exhibits flowers that are peach to melon in color with tangerine and pink highlights, 'SPd 06-11' exhibits flowers that are tomato red in color with a yellow-green throat, 'SPd 06-13' exhibits flowers that are light yellow in color, and 'SPd 06-16' exhibits flowers that are golden yellow in color with a gold-green throat.

BRIEF DESCRIPTION OF THE DRAWING

The accompanying colored photograph illustrates the overall appearance and distinct characteristics of the new *Hemerocallis*. The photographs were taken in early spring of a two year-old plant of 'SPd 06-12' as grown outdoors in a field plot from a single fan in McIntosh, Fla. without fungicide treatment, growth regulators or deadheading.

The photograph in FIG. 1 illustrates its early flowering, grass-like foliage, high bud counts, short scapes, and self-cleaning of blooms of 'SPd 06-12'.

Figure 1:
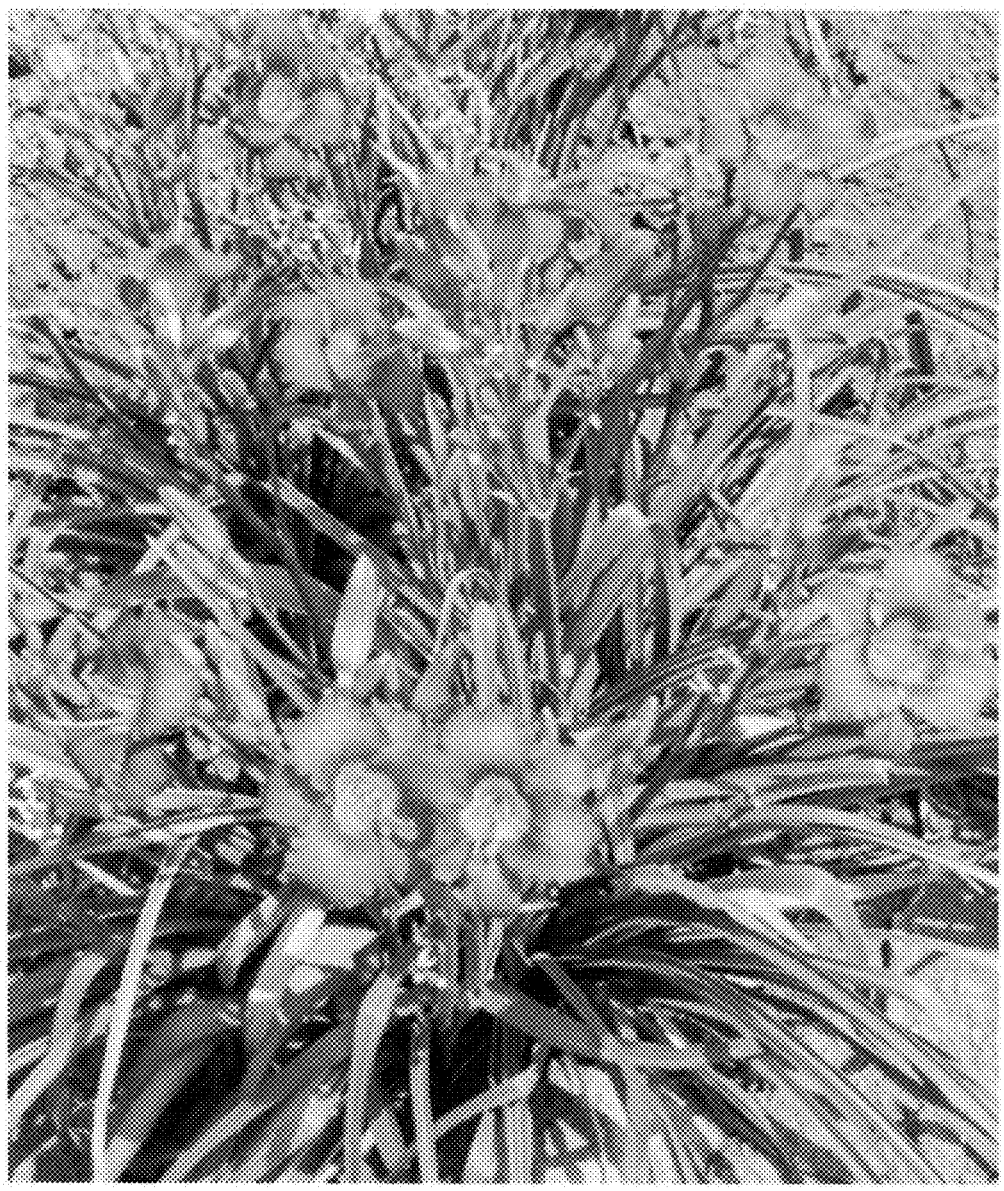
Figure 2:
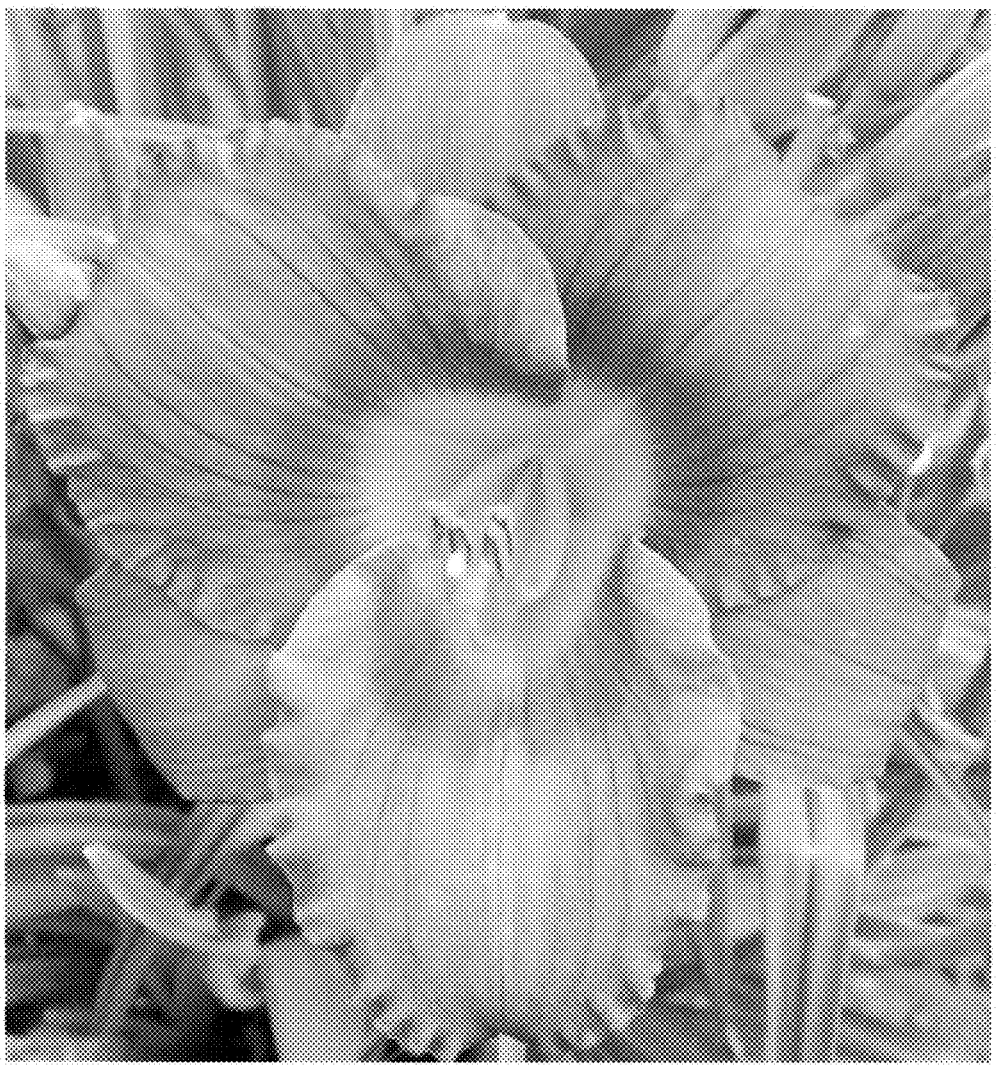

The photograph in FIG. 2 provides a close-up view of a flower of 'SPd 06-12'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of a 2 year-old plant of the new cultivar as grown outdoors in a 1-gallon container in McIntosh, Fla. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General characteristics:

*Blooming period.*—Commencing in March and recurrent until frost in Florida.

*Plant habit.*—Herbaceous perennial, compact grass-like foliage.

*Height and spread.*—Reaches about 30 to 40 cm in height and 30 cm in spread, flower scapes up to 40 cm in height.

*Hardiness.*—At least in U.S.D.A. Zones 4 to 11.

*Diseases and pests.*—Has been observed to be very tolerant to daylily rust (*Puccinia hemerocallidis*).

*Root description.*—Fibrous roots.

*Propagation.*—Division and tissue culture.

*Growth rate.*—Vigorous with a high multiplication rate (5 fans per fan per season).

Foliage description:

*Leaf shape.*—Linear.

*Leaf division.*—Simple.

*Leaf base.*—Sheathed to crown.

*Leaf apex.*—Narrowly acute.

*Leaf venation.*—Longitudinal, parallel, not prominent, same color as leaves.

*Leaf margins.*—Entire.

*Leaf attachment.*—Sheathed, not petiolate.

*Leaf arrangement.*—Equitant, fan-shaped.

*Leaf orientation.*—Held upright and slightly pendulant from mid section towards apex once matured.

*Leaf surface.*—Glabrous to slightly glaucous.

*Leaf color.*—Young leaves (upper and lower surface); a blend of 137C and 144A, mature leaves (upper and lower surface); a blend of 137B and 144A.

*Leaf size.*—Up to 60 cm in length, 2 cm in width.

*Leaf quantity.*—About 55 leaves per plant, 7 to 15 leaves per fan.

Flower scape description:

*Scape shape.*—Round, slightly ovoid, pithy.

*Scape number.*—1 per fan.

*Scape posture.*—Straight, held upright.

*Scape size.*—An average of 24 cm in length and 5 mm in width.

*Scape color.*—A blend of 137A and 137B.

*Scape surface.*—Glabrous, slight sheen.

*Scape branching.*—Typically 2 branches, v-branched (no internode).

*Scape leaves.*—1 per branch point, a blend of 144A and 137B in color, 4 to 7 cm in length, about 1 cm in width at base, sheathed base, acuminate apex, glabrous on both surfaces.

Flower description:

*Inflorescence type.*—Branched scape bearing a cluster of single flowers, 1 to 2 flowers open at a time.

*Inflorescence size.*—Varies with opening of flowers, an average of 13 cm in width and 9 cm in depth on per branch.

*Lastingness of flowers.*—About 24 hours, persistent.

*Flower size.*—Average of 5 cm in depth and 10 cm in diameter (excluding reproductive organs).

*Flower fragrance.*—None.

*Flower number.*—An average of 14 per branched scape.

*Flower aspect.*—Upright to outward.

*Flower bud.*—Oblong in shape, an average of 6.4 cm in length and 2.2 cm in width, color 16A and suffused with N34A and a blend of 145A and 145B at base.

*Petal number.*—3.

*Petal shape.*—Broadly elliptic, slightly recurved.

*Petal color.*—Upper surface; a blend of 68C and 54C with fine veins of N34A, eye zone N34A, throat 16B blending to N144C, lower surface; 16B and a blend of 68C, and N34A near upper portion and 144B near base.

*Petal surface.*—Glabrous, waxy, mid-vein raised in upper surface.

*Petal margins.*—Crenate, lightly ruffled.

*Petal apex.*—Obtuse.

*Petal size.*—An average of 6 cm in length and 3.6 mm in width.

*Sepal number.*—3.

*Sepal shape.*—Elliptic, recurved.

*Sepal margin.*—Entire.

*Sepal size.*—Average of 6.2 cm in length, 2.8 cm in width.

*Sepal surface.*—Glaucous.

*Sepal apex.*—Acute, cuneate.

*Sepal base.*—Fused.

*Sepals color.*—Upper surface; a blend of 68C and 54C with veins of N34A, base N144C, lower surface; 16B and a blend of 68C, and N34A near upper portion and 144B near base.

*Peduncles.*—An average of 4 cm in length and 3 mm in width, oval in shape, strong, color a blend of 137A and 137B.

*Pedicels.*—An average of 5 mm in length and 3 mm in width, oval in shape, strong and stout, color a blend of 137A and 137B.

Reproductive organs:

*Gynoecium.*—1 pistil, style; about 8 cm in length and 1.5 mm in width, 20A in color; stigma; minute, 20B in color, ovary; 0.6 cm in length, 4 mm in width, 138B in color.

*Androecium.*—6 stamens, anther; 9 mm in length, 2 mm in width, N200A in color; filament; 3.8 cm in length, 2 mm in width at base, 20A in color, pollen is moderate in abundant and 17A in color.

*Fruit/seeds.*—None observed.

It is claimed:

1. A new and distinct cultivar of *Hemerocallis* plant named 'SPd 06-12' as herein illustrated and described.

* * * * *